United States Patent
Le

(10) Patent No.: US 6,929,744 B2
(45) Date of Patent: Aug. 16, 2005

(54) SLUDGE TREATMENT AT A MESOPHILIC TEMPERATURE

(75) Inventor: Son Le, Pieston (GB)

(73) Assignee: United Utilites PLC, Warrington (GB)

(*) Notice: Subject to any disclaimer, the term of this patent is extended or adjusted under 35 U.S.C. 154(b) by 0 days.

(21) Appl. No.: 10/276,034

(22) PCT Filed: May 2, 2001

(86) PCT No.: PCT/GB01/01918
§ 371 (c)(1),
(2), (4) Date: Feb. 27, 2003

(87) PCT Pub. No.: WO01/85627
PCT Pub. Date: Nov. 15, 2001

(65) Prior Publication Data
US 2003/0155295 A1 Aug. 21, 2003

(30) Foreign Application Priority Data
May 12, 2000 (GB) .................................................. 0011470
Oct. 20, 2000 (GB) .................................................. 0025868

(51) Int. Cl.$^7$ ............................. C02F 11/04; C02F 3/28
(52) U.S. Cl. ..................... 210/603; 210/613; 435/262.5
(58) Field of Search ................................. 210/603, 612, 210/613, 175, 252, 259; 435/262, 262.5

(56) References Cited

U.S. PATENT DOCUMENTS

| | | | | |
|---|---|---|---|---|
| 2,029,702 A | * | 2/1936 | Buswell et al. | 210/603 |
| 2,198,737 A | * | 4/1940 | Petersen | 210/603 |
| 2,315,577 A | | 4/1943 | Hermann | |
| 2,528,649 A | * | 11/1950 | Genter et al. | 210/609 |
| 2,893,957 A | * | 7/1959 | Kennedy et al. | 210/603 |
| 3,640,846 A | | 2/1972 | Johnson | |
| 3,959,125 A | * | 5/1976 | Teletzke | 210/603 |
| 4,022,665 A | * | 5/1977 | Ghosh et al. | 435/167 |
| 4,026,793 A | * | 5/1977 | Rein | 210/613 |
| 4,214,985 A | * | 7/1980 | Bodenrader | 210/611 |
| 4,238,337 A | | 12/1980 | Peters et al. | |
| 4,297,216 A | * | 10/1981 | Ishida et al. | 210/613 |
| 4,396,402 A | * | 8/1983 | Ghosh | 48/197 A |
| 4,551,243 A | * | 11/1985 | Martin | 210/180 |
| 4,696,746 A | * | 9/1987 | Ghosh et al. | 210/603 |
| 4,735,724 A | | 4/1988 | Chynoweth | |
| 5,248,419 A | * | 9/1993 | Long et al. | 210/218 |
| 5,417,861 A | * | 5/1995 | Burnham | 210/609 |
| 5,525,229 A | * | 6/1996 | Shih | 210/603 |
| 5,599,450 A | * | 2/1997 | Li et al. | 210/603 |
| 5,651,890 A | * | 7/1997 | Trost | 210/603 |
| 5,670,047 A | * | 9/1997 | Burke | 210/603 |
| 5,746,919 A | * | 5/1998 | Dague et al. | 210/603 |
| 5,785,852 A | * | 7/1998 | Rivard et al. | 210/613 |
| 6,113,789 A | * | 9/2000 | Burke | 210/609 |
| 6,206,091 B1 | * | 3/2001 | Buehler | 165/143 |
| 6,325,935 B1 | * | 12/2001 | Hojsgaard | 210/609 |
| 6,521,133 B1 | * | 2/2003 | Roediger | 210/742 |

FOREIGN PATENT DOCUMENTS

| | | |
|---|---|---|
| EP | 0 172 070 | 2/1986 |
| EP | 0 263 796 | 4/1988 |
| GB | 1 522 780 | 8/1978 |
| GB | 2 050 339 | 1/1981 |
| GB | 2 284 413 | 6/1995 |
| WO | WO 84/00038 | 1/1984 |

OTHER PUBLICATIONS

WPI Abstract Accession, No. 1995–107376, CA 002098932, Balu.

(Continued)

*Primary Examiner*—Fred G. Prince
(74) *Attorney, Agent, or Firm*—Woodard, Emhardt, Moriarty, McNett & Henry LLP

(57) ABSTRACT

A method of treating sewage sludge comprises incubating raw sludge at a temperature in the mesophilic range to reduce the pathogen content of the sludge.

9 Claims, 3 Drawing Sheets

OTHER PUBLICATIONS

WPI Abstract Accession, No. 1986–225944, DD000235249, ZBE Futtermitt.

Wilson, Two Phase Anaerobic Digestion: An Assessment, Proc. 12th Annual Residuals and Biosolids Management Conference WEF, pp. 195–203, Jul. 1998.

Winfield, et al., Innovative Digestion and Baltimore, WEFTEC, 2000.

Ghosh, et al., Two–Phase Fermentation: An Innovative Approach To Gasification of Biosolids Resources, pp. 10–31 though 10–37.

Roberts, PhD Thesis "An Evaluation of Anaerobic Thermophilic/Mesophilic Dual Digestion of Sludge", University of Birmingham, Sep. 1998.

Bolton, Sewage Treatment Basic Principles and Trends, 2nd Edition, Butterworths, pp. 128–133, 1971.

Brooks, Conversion of Sludge into Utilisable Gas, pp. 55–58, 63, 67, 1974.

* cited by examiner

SLUDGE TREATMENT AT A MESOPHILIC TEMPERATURE

The present invention relates to a method and apparatus for the treatment of sewage sludge.

Sewage sludge is widely used in the agricultural industry as a source of fertiliser and soil conditioner. To render raw sewage sludge suitable for such use, it must first be treated both to reduce the organic content to stabilise the sludge and also to reduce the pathogen content.

A well known traditional sewage sludge treatment process is mesophilic anaerobic digestion (MAD) which reduces the organic content of sewage sludge by conversion to methane through the actions of micro-organisms. In practical processes small volumes of raw sludge are fed to a reactor vessel containing a much larger volume of digested sludge (within which the necessary ecology has been established and is maintained) displacing a similarly small volume of digested sludge in the process. This may either be a continuous process or a batch process, but whichever method is operated the amount of raw sludge introduced to the reactor has to be relatively small in comparison to the volume of the reactor to ensure that the necessary conditions for the ongoing digestion are maintained. Raw sewage introduced into the reactor is thoroughly mixed and the average time any particular volume of sewage spends in the reactor is referred to as the retention time.

The processes which occur in a traditional MAD process are well documented. Essentially the digestion process is considered to involve three steps: a first step of solubilisation of solids by enzymes; a second step of bacterial synthesis of fatty acids (acidogenesis); and finally a third step of gasification by the methane bacteria. A temperature of 30°–35° C. provides the best rate of conversion and stability with a typical retention time of at least 12 days and typically of the order of 18–20 days.

It has in the past been considered that sufficient sludge stabilisation and pathogen reduction could be achieved by treating the sludge in a MAD process comprising a primary digestion stage carried out in a stirred reactor for a retention period of around twelve days at a temperature of approximately 35° C. followed by a secondary digestion in an unstirred tank for a further period of around fourteen days. However, in more recent times, particularly in the wake of increasing concern over well publicised problems relating to sewage-borne diseases such as BSE and *E.coli*, the level of pathogen reduction that can be achieved in such MAD processes alone is no longer considered sufficient to meet health requirements.

Commercial disinfection processes are known which can produce levels of pathogen reduction sufficient to meet the increasingly stringent requirements. In general, such processes rely on high temperatures to pasteurise the sewage and thereby effect pathogen deactivation. Typical processes require holding the sewage at a minimum temperature of around 55° C. for at least twenty four hours. More usually, commercial processes operate at a higher temperature to reduce the required time. For instance, there are commercial systems which operate at 65° C. for one hour or 72° C. for thirty minutes. As mentioned above the minimum temperature required for the de-naturation of proteins and DNA considered necessary for effective pathogen reduction is 55° C.

As a result of the above, conventional methods currently employed for the treatment of sewage comprise two stages: a first pasteurisation stage to reduce pathogen content and a second stabilisation stage to reduce organic content. The most widely used method of sewage sludge treatment which has been operating for a number of years is such a dual stage process in which the first stage comprises thermophilic aerobic digestion (TAD) and the second stage comprises MAD process. The initial TAD stage relies on a combination of thermophilic aerobic digestion and hot water to establish the temperature necessary to produce the required levels of pathogen reduction. Details of this type of system, and the nature of the reactions occurring, are well known and well documented.

It has also been suggested that a MAD process may be split into a two stage process with a first stage operated at a temperature between 55°–60° C. to achieve disinfection. This process operated in a laboratory environment is described in the PhD thesis of R. Roberts, (University of Birmingham, 1998). The motivation for splitting the MAD process into two stages in this case was not to increase pathogen reduction but rather to improve the anaerobic digestion and promote methane production. The first stage process is an acidogenesis process operated at pH5, at a temperature of 55°–65° C., in order to maximise acid production whilst simultaneously achieving disinfection (pathogen deactivation). The acidic product from the first stage was continuously fed to a second stage methanogenesis operated at pH 7.5 at a conventional mesophilic temperature of around 35° C. Although improved methane yield was claimed, there was no report on the level of pathogen reduction achieved. Moreover the process is difficult to stabilise because of the need to balance the acid and methane production and this process has had no subsequent practical application.

Two stage sludge treatment processes requiring a first thermal disinfection stage inevitably require a substantial investment in reactor vessels, mixing/aeration devices and heat delivery systems. It is therefore relatively expensive to establish such processes and also expensive to provide the necessary power and heat to maintain their operation. It is an object of the present invention to obviate or mitigate these disadvantages.

According to a first aspect of the present invention there is provided a process for the disinfection of sewage sludge comprising the step of incubating raw sludge at a temperature in the mesophilic range.

The present inventor has established that incubation of raw sewage sludge in an incubator maintained at a temperature within the mesophilic range can produce very good pathogen reduction.

The present invention thereby provides a microbial incubation process (MIP) which may be used to disinfect sludge prior to a conventional digestion. The simplicity and low operating temperature of the MIP process provides significant operational and cost benefits.

The mesophilic temperature range is conventionally understood to be from about 25° C. to about 45° C. Although as is discussed further below temperature is not believed to be the direct cause of the pathogen reduction it can have an effect on the rate of pathogen reduction and in the present invention the preferred operating temperature range is between 32° C. and 42° C.

Also as mentioned further below, the term "raw" should be interpreted broadly as referring to sewage sludge having a high organic content. Typically this will be sludge having a total Chemical Oxygen Demand (COD) greater than about 10,000 mg/l, although in practical applications the sludge of interest is likely to have a COD in the range 30,000 to 500,000 mg/l and a BOD (5 day) in the range 8,000 to 250,000 mg/l (the BOD indicating the biodegradalility of the sludge).

The incubation period may be varied, for instance depending on the required level of pathogen reduction. The present invention has provided very good pathogen reduction levels with incubation periods down to about twelve hours. A typical incubation period may be between 1 and 4 days, it being unlikely that it would be necessary to incubate for more than seven days to achieve good pathogen reduction.

As mentioned above conventional MAD processes alone provide very poor disinfection. The degree of pathogen reduction is normally measured on a log scale, a log 1 reduction being a tenfold reduction, a log 2 reduction being a hundred fold reduction etc. Sludge digested in a conventional MAD reactor typically shows a log reduction of the order of 1.5. Given the relatively low temperature at which MAD processes operate (i.e. the mesophilic temperature range of 25 to 45° C. which is well below the 55° C. minimum temperature generally considered necessary for thermal dissinfection) what little pathogen reduction does occur is assumed to be a result of natural dying off processes. It has also been noted that the degree of pathogen reduction in a conventional MAD process can be quite variable, typically varying between a log reduction of 0 and a log reduction of 3. This variation is assumed to be a result of variations in the effectiveness of the mixing operations taking place in the MAD reactor and even the bypass of raw sewage sludge directly from the reactor inlet to the reactor outlet.

The present inventor has however established that very good levels of pathogen reduction, much higher than those achieved in conventional MAD processes, can be achieved at mesophilic temperatures by incubating raw sludge rather than the partially digested sludge which is maintained in a conventional MAD reactor. Indeed, the method of the present invention has achieved a log reduction in pathogen content much greater than log 3.

Clearly the temperature alone is not responsible directly for the deactivation of pathogens since the same temperature is used in conventional MAD reactors and is well below the accepted minimum of 55° C. required for thermal dissinfection. Moreover, 37° C., which is one possible operating temperature of the present invention, is the ideal growing temperature for pathogens such as *E.coli*.

Further consideration of the digestion processes occurring in sludge at mesophilic temperatures has led the inventor to the current belief that the pathogen deactivation is a direct result of the action of enzymes secreted by spoilage bacteria which is naturally present in the sludge and which is responsible for the initial solubilisation of organic solids in the sewage sludge. It is thought that amongst the host of enzymes secreted by the spoilage bacteria to break down the different food groups are enzymes which destroy the pathogens such as *E.coli*. The details of the process are not yet fully understood and the inventor does not therefore wish to be bound by the current understanding as set out above and discussed further below. Nevertheless, this does offer an explanation as to why good pathogen reduction occurs in the MIP processes of the present invention but no significant pathogen reduction occurs in conventional MAD processes.

In particular, the present invention seeks to optimise the conditions for establishing a high population of the spoilage bacteria. A significant factor contributing to this is the availability of organic matter on which the spoilage bacteria primarily feeds. With the present invention the incubation of raw sludge ensures a high organic content which promotes the growth of the spoilage bacteria and thus the consequent reduction in pathogen content. With conventional MAD processes, however, the reactor contains a high proportion of digested sludge (necessary to maintain the ecology required for good methane production) so that the overall organic content of the reactor is low. This depletion of the available food source for the spoilage bacteria limits growth of the spoilage bacteria which therefore has no significant effect on the pathogen content. Although conventional MAD reactors are fed with raw sludge (i.e. sludge with a high organic content) this takes place in relatively small amounts (relative to the size of the reactor), either in batches or continuously, and the food source present in the raw sludge is mixed and therefore diluted in the digested sludge. Thus, the traditional feed regime for conventional MAD reactors is currently considered largely responsible for the poor pathogen reduction performance.

Another factor which is considered to contribute to the effective pathogen reduction of the present invention is that the raw sludge is initially at a relatively low pH of around pH 5 to pH 6.5. The spoilage bacteria is particularly active at these pH ranges. In a conventional MAD reactor the pH will be higher (of the order of pH 7 to pH 8) as a result of ammonia production. The pH of the raw sludge treated in accordance with the present invention will increase as a result of the incubation process but nevertheless high levels of pathogen reduction are achievable.

It will be understood that whereas the term "raw" sewage sludge normally refers to a sludge stream resulting directly from a sewage treatment process the present invention can be used to treat any sludge stream containing harmful pathogens such as farmyard slurries, abattoir wastes and wastes from other industrial processes. Moreover, the term "raw" is used to refer to a sludge which has a relatively high organic content and does not exclude the possibility that there has been some degree of pre-treatment on the sludge.

The process according to the present invention can be used to reduce the pathogen content of sludge which is subsequently treated by a conventional MAD process to stabilise the organic content. In this case only the primary MAD stage is required and the secondary digestion mentioned above is obviated. The spoilage bacteria will not itself be a problem as it will naturally die off particularly in the high pH conditions and the lack of food in the MAD reactor.

For instance a practical implementation of the MIP process in accordance with the present invention may be carried out in an incubator upstream of a conventional MAD reactor. Batches of raw sludge may for example be incubated and delivered as a whole to the MAD reactor. Since the incubation takes place at mesophilic temperatures it will not be necessary to cool the sludge before feeding it to the MAD reactor which is a further advantage of the invention.

According to a second aspect of the present invention there is provided an incubation vessel for incubating sewage sludge having an inlet for receiving raw sludge to be treated and an outlet for discharging treated sludge after a predetermined retention period, means for discharging gas generated by the incubation process, and means for maintaining the incubation vessel at a temperature within the mesophilic temperature range to reduce the pathogen content of the sludge.

The MIP process may be performed in a relatively simple incubator comprising little more than a tank to hold the sludge at the required temperature for the required retention period. In this case, it would not be desirable to continuously pass sludge through the incubator to, for instance, a downstream MAD reactor because of the potential problem of raw sludge by-passing directly from the input to the output of the incubator before sufficient pathogen reduction has taken place. However, a continuous flow of sludge can be obtained by incubating the sludge in a "plugflow" reactor.

Plugflow reactors are used in some chemical process industries to avoid the problem of feed by-passing. In such reactors there is a continuous input/output to/from the reactor but the material input to the reactor is at no stage mixed with material already present in the reactor. The result is that all material passes through the reactor with the same residence time (assuming the overall flow rate through the rector is steady). Such plugflow reactors have not previously been used for sewage treatment as they are not practical for use as conventional MAD reactors in which a stable microbial ecology must be established—the operation of a plugflow reactor would result in the displacement of the necessary ecology. However, the incubation process according to the present invention requires no such ecology and this, together with the relatively short retention time required for the incubation process, makes plugflow reactors an idea form of reactor for the incubation process.

It is not however, possible to use conventional plugflow reactors for the incubation process because conventional plugflow reactors are designed for use with a single phase material, i.e. liquid only. In the present instance the incubation generates biogas which must be separated from the sludge if the plugflow characteristics are to be preserved.

Thus, according to a preferred embodiment of the present invention the incubation vessel has plugflow characteristics such that the retention time of each portion of sludge within the reaction vessel is a function of the sludge flow rate through the vessel so that for a given sludge flow rate all sludge has substantially the same retention time.

It will be appreciated that the downstream process for stabilising the sludge need not necessarily be a MAD process and any other suitable process could be used to reduce the organic content of the sludge.

Specific embodiments of the present invention will now be described, by way of example only, with reference to the accompanying drawings, in which.

Figure 1:
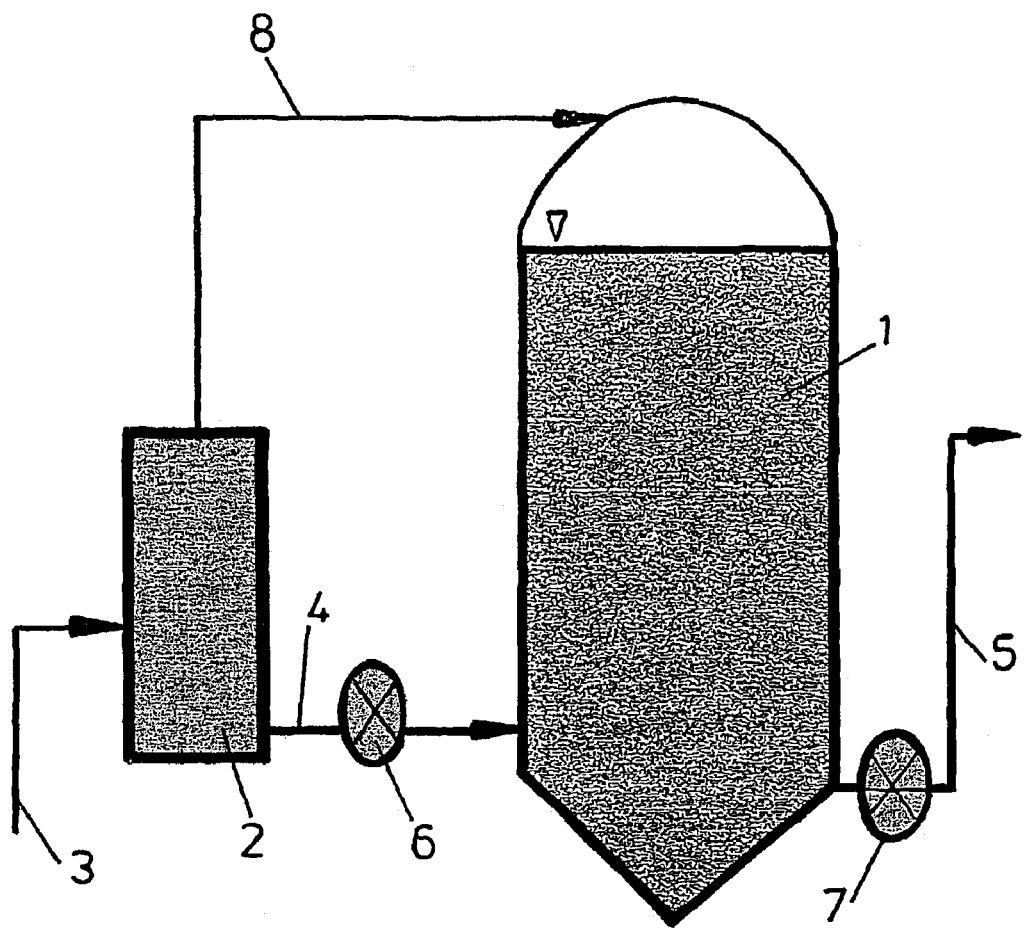
FIG. 1 is a schematic illustration of sewage sludge treatment apparatus in accordance with a first embodiment of the present invention.

Referring to FIG. 1, reference 1 represents a conventional MAD reactor. Reference 2 is an incubator for incubating raw sewage sludge in accordance with the present invention. The incubator has an inlet line 3 and an outlet line 4 which feeds to the inlet of the digester 1. The digester 1 has an outlet line 5. Flow through lines 4 and 5 is controlled by valves 6 and 7. There is a further line 8 for supplying biogas generated in the incubator to the head region of the digester 1 from where it can be collected together with biogas generated by the MAD process (thus avoiding the need for separate gas collection tank).

In accordance with the present invention raw sludge is fed to, and held within, the incubator and maintained at a temperature within the mesophilic range during an incubation period of preferably between 0.5 and 7 days. Once incubated the raw sludge is fed to the digester via valve 5. The digester functions in conventional manner, effectively operating in batch feed mode receiving batches of sludge from the incubator.

The incubator need only be a small vessel and may be heated by way of the existing heat system needed to maintain the temperature within the digester (typically a hot water system). Accordingly, very little additional running costs are involved, particularly as the incubator does not require any mixing or aeration as is typically required in a digester. It should also be born in mind that some organic conversion will take place during the incubation and thus the retention time of the digester may be reduced accordingly without any reduction in the overall hydraulic retention time of the sludge in the treatment process as a whole. The overall rate of throughput need not therefore be reduced by the preliminary incubation process.

The effectiveness of the present invention is demonstrated by the following examples.

EXAMPLE 1

Two samples of raw sewage sludge with 4.65% dry solids content; 71,000 mg/l COD (Chemical Oxygen Demand); 20,700 mg/l BOD (5-day Biochemical Oxygen Demand, i.e. ease of biodegradation) and pH5.6 were incubated in closed vessel at 20° C. and 35° C. respectively for five days. The pathogen level in the samples was monitored daily over the period. The results are given in Table 1.

TABLE 1

| Log reduction of *E. coli* in raw sludge by incubation | | |
| --- | --- | --- |
| Day number | At 20° C. | At 35° C. |
| 1 | 0.2 | 0.8 |
| 2 | 0.5 | 1.5 |
| 3 | 0.7 | 2.5 |
| 5 | 1.1 | 5.0 |

These results demonstrate that the rate of pathogen reduction can be increased by incubating the sludge at higher temperatures within the mesophilic temperature range despite the fact that such temperatures are close to the optimum temperature for growth of *E.coli*.

EXAMPLE 2

Raw sludge as in example 1 was fed in batches of 100 m$^3$ to a mesophilic anaerobic digester of 1800 m$^3$ volume on a daily basis. Upon addition of the raw sludge the same volume of digested sludge was displaced from the digester. At steady state it was found that the level of *E. coli* in the raw sludge was about 32 times the level in the digested sludge, i.e. there has been a 1.5 log reduction in the pathogen level in the digester. This demonstrates that mesophilic temperature alone is not responsible for the high level of pathogen reduction attainable with the present invention.

EXAMPLE 3

Two samples of digested sludge were spiked with small amounts of raw sewage sludge to raise the pathogen level. The digested sludge has the following characteristics: 4.05% dry solids content; 36,000 mg/l COD; 1,400 mg/l BOD and pH7.5. The samples were again incubated in closed vessels at 20° C. and 35° C. respectively for a period of five days. As with example 1 the pathogen level in the samples was monitored daily over the period. The results are given in Table 2.

TABLE 2

Log reduction of E. coli in digested sludge by incubation

| Day number | At 20° C. | At 35° C. |
|---|---|---|
| 1 | 0.1 | 0.2 |
| 2 | 0.3 | 0.4 |
| 3 | 0.5 | 0.7 |
| 5 | 0.8 | 1.3 |

This demonstrates that the high levels of pathogen reduction achieved by incubating raw sludge in accordance with the present invention cannot be achieved by incubating partially digested sludge under the same conditions.

EXAMPLE 4

Example 2 was repeated, but this time the raw sludge was incubated in a closed vessel for 3 days at 35° C. before it was fed to the digester. At steady state it was found that the level of *E. coli* in the raw sludge was about 10,000 times the level in the digested sludge, i.e. there has been a 4 log reduction in the pathogen level in the combined incubator and digester treatment.

EXAMPLE 5

Samples of raw sewage sludge with 7.5% dry solids content; 108,000 mg/l COD (Chemical Oxygen Demand); 5,700 mg/l sCOD (soluble Chemical Oxygen Demand) and pH5.8 were treated with acetic acid and lime to pH4.0 and pH10.0 respectively. The samples were incubated in closed vessels at 20° C. for a period of time. The pathogen level in the samples was monitored over the period. The results are given in Table 3.

TABLE 3

Log reduction of E. coli in raw sludge by incubation at 20° C.

| Day number | Untreated (pH 5.6) | Acidified (pH 4.0) | Limed (pH 10.0) |
|---|---|---|---|
| 1 | 0.2 | 2.4 | 1.0 |
| 2 | 0.5 | 4.5 | 1.5 |
| 3 | 0.7 | 7.1 | 2.0 |
| 5 | 1.1 | 7.1 | 4.0 |

EXAMPLE 6

A sample of raw sewage sludge as in example 5 was incubated in closed vessel at 40° C. for 5 days. During the incubation period the sample was monitored for a number of parameters. The results are given in Table 4.

TABLE 4

Performance of the incubator at 40° C.

| Day number | E. coli (cfu/100 ml) | Salmonella (cfu/100 ml) | pH | Ammonia (mg/l) |
|---|---|---|---|---|
| 0 | 24,060,000 | 499 | 5.8 | 746 |
| 1 | 4,939,000 | 172 | 6.4 | 1037 |
| 2 | 6,061 | <18 | 6.6 | 1291 |
| 3 | 0 | 0 | 6.7 | 1414 |
| 4 | 0 | 0 | 6.6 | 1422 |
| 5 | 0 | 0 | 6.5 | 1463 |

EXAMPLE 7

After incubation as in example 6, the incubated sludge was fed in batches of 100 m$^3$ to a mesophilic anaerobic digester of 1800 m$^3$ volume on a daily basis. At steady state it was found that the level of biogas production was increased substantially compared to digesters which were fed with untreated sludge.

EXAMPLE 8

After incubation as in example 6, the incubated sludge was fed in batches of 25 m$^3$ to a Thermophilic Aerobic Digester of 25 m$^3$ volume every 5 days. At steady state it was found that the level of heat production was increased substantially compared to digesters which were fed with untreated sludge.

In the simple system schematically illustrated in FIG. 1 the incubator 1 is relatively unsophisticated and must be operated in batch mode to avoid the unwanted possibility of raw sludge passing from the inlet 3 to the outlet 4 before sufficient pathogen reduction has occurred. However, as mentioned above, the present invention is ideally suited to the use of appropriately designed pluflow reactors. Two examples of embodiments of plugflow reactors in accordance with the present invention are schematically illustrated in FIGS. 2 and 3 respectively.

Figure 2:
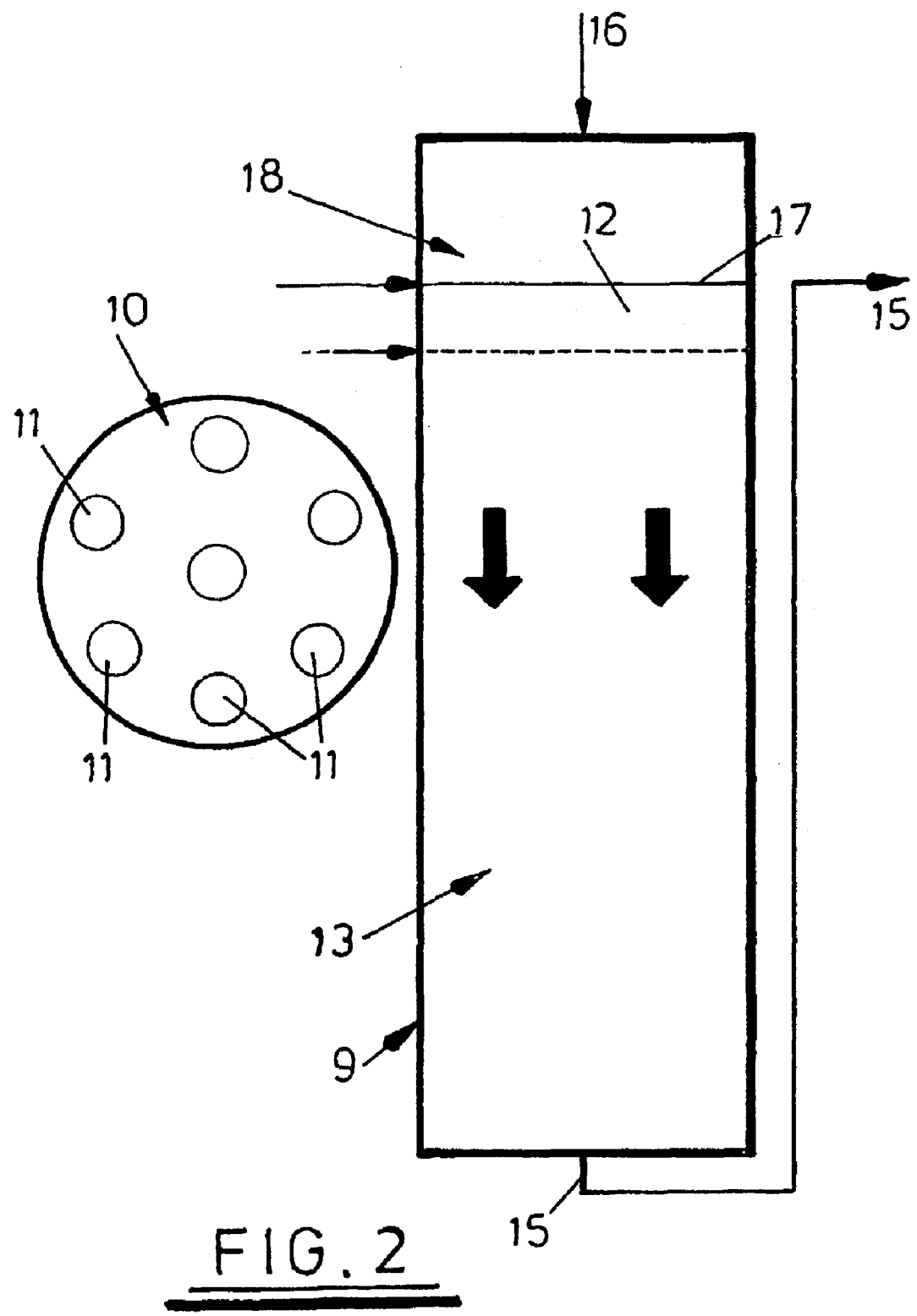
FIG. 2 is a schematic illustration of a first plugflow reactor which may be used as an incubator in a method according to the present invention.
Figure 3:
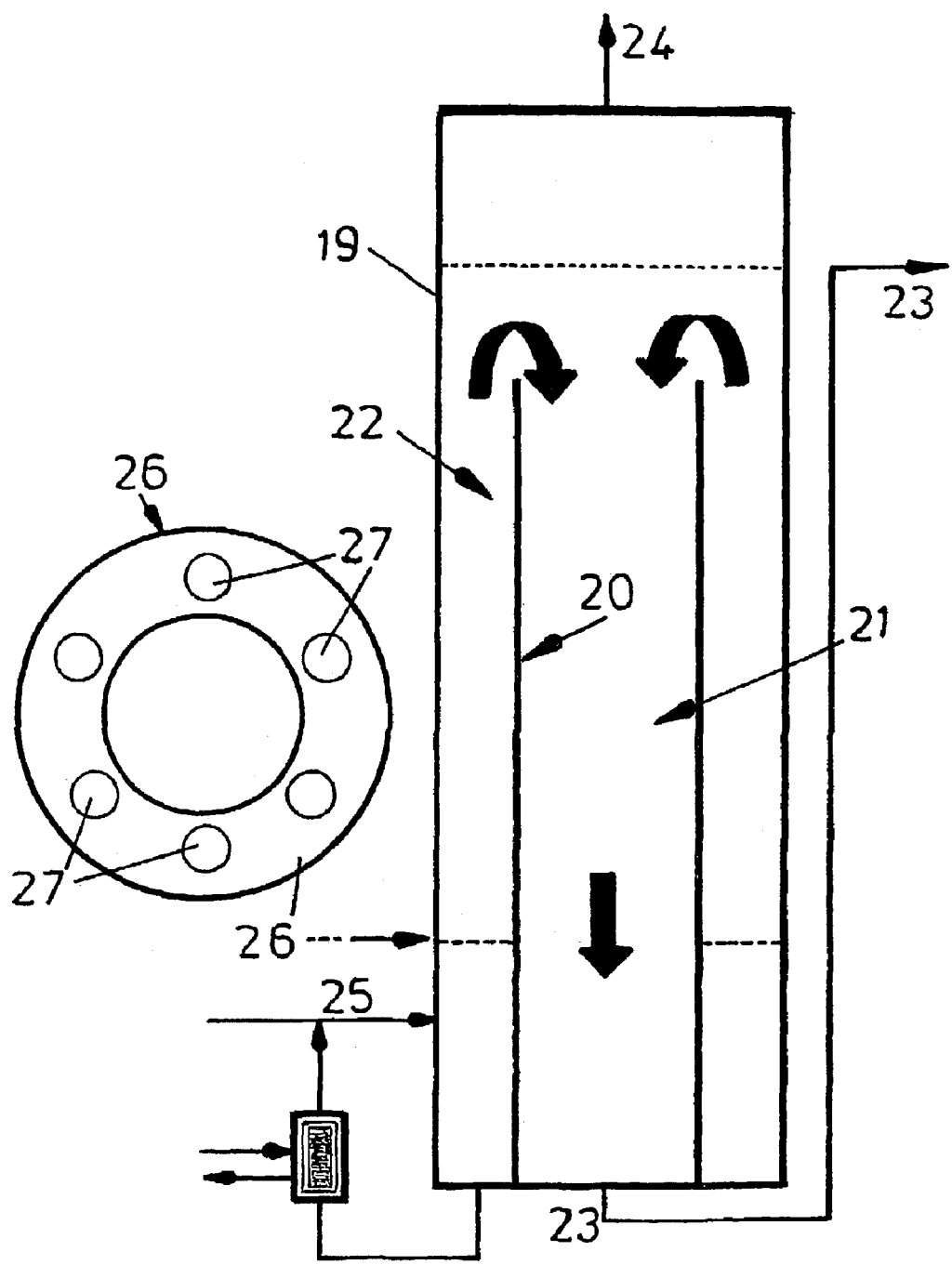
FIG. 3 is a schematic illustration of a second plugflow reactor which may be used as an incubator in a method according to the present invention.

Referring first to FIG. 2, this illustrates a generally cylindrical reactor 9 which is divided internally by a flow distributor 10 positioned about ¾ of the way up the reactor (the position is not critical). The flow distributor 10 is a circular disc provided with seven spaced apertures 11 which divides the reactor 9 into an upper inlet chamber 12 and a lower chamber 13. An inlet line 14 is provided for feeding raw sludge into the inlet chamber 12 and an outlet line 15 is provided at the bottom of the reactor 9 for removing sludge from the bottom of the chamber 13. A biogas vent line 16 is provided at the head of the reactor 9 (which may discharge the biogas to a gas collection tank or to a downstream MAD reactor etc).

In use, raw sludge is fed to the reactor 9 (which is maintained at a mesophilic temperature) via the inlet 14 and thus enters the inlet chamber 12 immediately above the flow distributor 10. The inlet chamber 12 however is not completely filled with raw sludge, for instance being filled only to the level of the inlet 14 as indicated by the line 17. This leaves a head space 18 above the sludge within which the biogas given off by the sludge may collect to be vented off via the biogas vent line 16.

As sludge is fed to the reactor 9 via the inlet line 14 the flow distributor 10 promotes spreading of the sludge across the full width of the reactor 9. From the inlet chamber 12 the sludge falls under gravity through the apertures 11 in the flow distributor 10 and drops downwardly through the main reactor chamber 13 at a rate controlled by the rate at which sludge is drawn off from the bottom of the reactor via the outlet 15. The arrangement ensures that there is no significant mixing between the raw sludge input into the reactor and sludge already present within the reactor. The process can therefore be continuous with all sludge input into the reactor 9 having substantially the same retention time within the reactor as it falls to the outlet 15

Since the biogas generated by the hydrolysis occurring within the reactor flows upwardly to the head space 18, i.e. in contraflow to the direction of flow of the sludge, back infection of the treated sludge by the biogas is avoided. In addition, by positioning the sludge outlet 15 at the bottom of the main reactor chamber 13 any settlements from the sludge will be carried out with the flow rather than accumulating within the reactor 9.

It will thus be seen that a continuous flow of incubated sludge can be obtained using a relatively simple reactor construction which provides plugflow characteristics. It will be appreciated that a number of modifications could be made to the reactor illustrated in FIG. 2. For instance, the exact form of the flow distributor could vary widely. Indeed, the flow distributor could be dispensed with alltogether by providing a plurality of spaced inlets around the reactor positioned to distribute input sludge evenly across the full width of the reactor.

One possible alternative design of a plugflow reactor in accordance with the present invention is illustrated in FIG. 3. This illustrates a modified reactor 19 which has an external configuration similar to that of FIG. 1 but provides a longer flow path. Internally the reactor 19 has a central cylindrical wall 20 extending upwardly from the bottom of the reactor and terminating about ¾ of the way up the height of the reactor (this height is not critical) which defines a central cylindrical chamber 21 surounded by an outer annular chamber 22. The reactor 19 has an outlet 23 which is positioned at the bottom of the cylindrical chamber 21 and a biogas vent 24 at the head of the reactor. With this embodiment the sludge inlet 25 is positioned towards the bottom of the reactor for introducing sludge into an inlet portion of the annular chamber 22 defined immediately below an annular flow distributor 26. The modified flow distributor 26 comprises an annular ring provided with a number of circumferentially spaced apertures 27 which extend between the main reactor wall and the inner cylindrical wall 20.

The arrangement is such that sludge entering to the reactor inlet 25 initially flows upwards from the inlet portion of the annular chamber 22, through the flow distributor 26, until it reaches the top of the cylindrical wall 20. The sludge then falls through the central cylindrical chamber 21 towards the outlet 23. The input/output rates can be controlled to maintain the level of the sludge within the reactor 9 sufficiently below the top of the reactor to provide head space for the biogas to collect but so as to ensure that the cylindrical wall 20 is always submerged.

An optional sludge recirculation port 28 is illustrated which can be used to recirculate sludge from the inlet portion of the annular chamber 22 below the flow distributor 26 to the inlet 25 via a heat exchanger 29 for heating sludge to the required mesophilic temperature. Thus, sludge could initially be input into the reactor 9 cold.

The effectiveness of the present invention performed in plug flow reactors in accordance with FIGS. 2 and 3 is demonstrated by the following example.

EXAMPLE 9

A plug flow reactor as shown in FIG. 2 having a working volume of 2000 ml was used to treat raw sludge. The raw sludge was passed continuously through the reactor at a temperature of 40° C. and at a rate of 600 ml per day. Treated sludge was fed to a mesophilic anaerobic digester having a working volume of 10,000 ml. It was found that after anaerobic digestion the *E.coli* content of the sludge had been reduced by 1,000 fold compared to a 100 fold reduction if the sludge was not pre-treated in the plug flow reactor before delivery to the digester.

EXAMPLE 10

The plug flow reactor as illustrated in FIG. 3 having a working volume of 2000 ml was used to treat raw sludge. The reactor was immersed in a water bath maintained at a constant temperature of 42° C. and raw sludge pre-heated to a temperature of 10° C. was passed continuously through the reactor at the rate of 600 ml per day. After passing through the reactor the sludge temperature rose to 42° C. and was then fed to a mesophilic anaerobic digester having a working volume of 10,000 ml. It was found that after anaerobic digestion the *E.coli* content of the sludge was reduced by 2,500 fold (again compared a 100 fold reduction obtained if the sludge was not pre-treated in the plug flow reactor).

It will again be appreciated that many modifications could be made to the reactor illustrated in FIG. 3. For instance, the flow distributor 27 could also be replaced by a number of inlets distributed around the periphery of the reactor and the precise dimensions and relative positioning of the flow distributor, and the inner cylindrical wall may vary.

Other possible modifications of the illustrated reactors will be readily apparent to the appropriately skilled person.

What is claimed is:

1. A method of pre-treating organic waste sludge prior to a treatment for reduction of its organic content, the method of pre-treatment comprising the step of incubating substantially non-diluted raw sludge at a temperature in the mesophilic range of between 25 and 45 degrees centigrade for a period in the range of about 1 day to about 4 days to thereby reduce the pathogen content of the raw sludge.

2. The method according to claim 1, wherein the sludge is incubated in an incubator maintained at a temperature between 32 and 42 degrees centigrade.

3. The method according to claim 1, wherein the sludge is incubated in an incubation vessel provided with means for collecting and discharging biogas generated during incubation of said sludge.

4. The method according to claim 3, wherein the incubation vessel has plugflow characteristics.

5. The method according to claim 4, wherein the raw sludge is continuously fed to the incubation vessel and incubated sludge is continuously discharged from the incubation vessel, the rate of input and discharge from the incubation vessel being controlled to ensure that each portion of the sludge introduced into the vessel remains within the vessel for a predetermined period.

6. The method according to claim 1, further comprising the step of treating the sludge to reduce its organic content.

7. The method according to claim 6, wherein said further step comprises digesting the sludge by a process of mesophilic anaerobic digestion.

8. The method according to claim 7, wherein the pretreatment pathogen reduction step is performed in a first incubation vessel, and a second digestion step is performed in a second vessel the raw sludge being delivered to the first vessel for incubation and the incubated sludge being delivered from incubation vessel to the second vessel following said incubation.

9. The method according to claim 8, wherein the second vessel is a conventional MAD digester.

* * * * *